US010391123B2

(12) United States Patent
Liu et al.

(10) Patent No.: US 10,391,123 B2
(45) Date of Patent: *Aug. 27, 2019

(54) ANTICANCER NANO-SILVER COMPOSITION FOR TREATMENT AND PREVENTION OF CERVICAL CANCER, AND PREPARATION METHOD AND USE THEREOF

(71) Applicant: CHANGSHA DIGU NANO BIOTECHNOLOGY CO., LTD., Changsha (CN)

(72) Inventors: Jinjun Liu, Changsha (CN); Weiyi B. H. Situ, Changsha (CN); Qiangbai Li, Changsha (CN)

( * ) Notice: Subject to any disclaimer, the term of this patent is extended or adjusted under 35 U.S.C. 154(b) by 29 days.

This patent is subject to a terminal disclaimer.

(21) Appl. No.: 15/330,334

(22) PCT Filed: Mar. 27, 2015

(86) PCT No.: PCT/CN2015/000211
§ 371 (c)(1),
(2) Date: Sep. 7, 2016

(87) PCT Pub. No.: WO2015/143928
PCT Pub. Date: Oct. 1, 2015

(65) Prior Publication Data
US 2017/0266229 A1    Sep. 21, 2017

(30) Foreign Application Priority Data

Mar. 28, 2014 (CN) .......................... 2014 1 0122850

(51) Int. Cl.
| | |
|---|---|
| A61K 33/38 | (2006.01) |
| A61K 47/18 | (2017.01) |
| A61K 47/26 | (2006.01) |
| A61K 47/32 | (2006.01) |
| A61K 9/00 | (2006.01) |
| A61K 9/14 | (2006.01) |

(52) U.S. Cl.
CPC ............ *A61K 33/38* (2013.01); *A61K 9/0034* (2013.01); *A61K 9/14* (2013.01); *A61K 47/18* (2013.01); *A61K 47/26* (2013.01); *A61K 47/32* (2013.01)

(58) Field of Classification Search
CPC ........ A61K 9/14; A61K 9/0034; A61K 47/18; A61K 47/32
See application file for complete search history.

(56) References Cited

U.S. PATENT DOCUMENTS

| | | | |
|---|---|---|---|
| 2003/0185889 A1* | 10/2003 | Yan ........................ | A01N 59/16 424/484 |
| 2005/0008861 A1* | 1/2005 | Yadav ...................... | C08K 3/08 428/403 |
| 2011/0262556 A1* | 10/2011 | Holladay ............... | A01N 59/16 424/616 |

OTHER PUBLICATIONS

"prevent." Macmillandictionary.com. Macmillian, 2019. Web. Mar. 18, 2019. (Year: 2019).*
NHS. "Prevention Cervical Cancer". Retrieved on Mar. 18, 2019. Retrieved online <URL: https://www.nhs.uk/conditions/cervical-cancer/prevention/; pp. 1-3. (Year: 2019).*

* cited by examiner

*Primary Examiner* — Doan T Phan
(74) *Attorney, Agent, or Firm* — Panterrain IP Law; Charles Liu

(57) ABSTRACT

The present invention provided an anticancer nano-silver composition for the treatment and prevention of cervical cancer. The composition contains nano-silver powder 3-200 mg/kg, carbomer 700-1000 mg/kg, triethanolamine 700-1000 mg/kg, glucose 2.8-3.2 g/kg, and water as remaining; of the nano-silver powder, wherein the purity of silver is ≥99.99% and particle size is 1-5 nm. Experiments demonstrated that the anticancer nano-silver composition can be used to inhibit HeLa proliferation, and cause cell death. The anticancer nano-silver composition of the present invention can be used to manufacture medicaments for the treatment and prevention of cervical cancer.

3 Claims, 1 Drawing Sheet

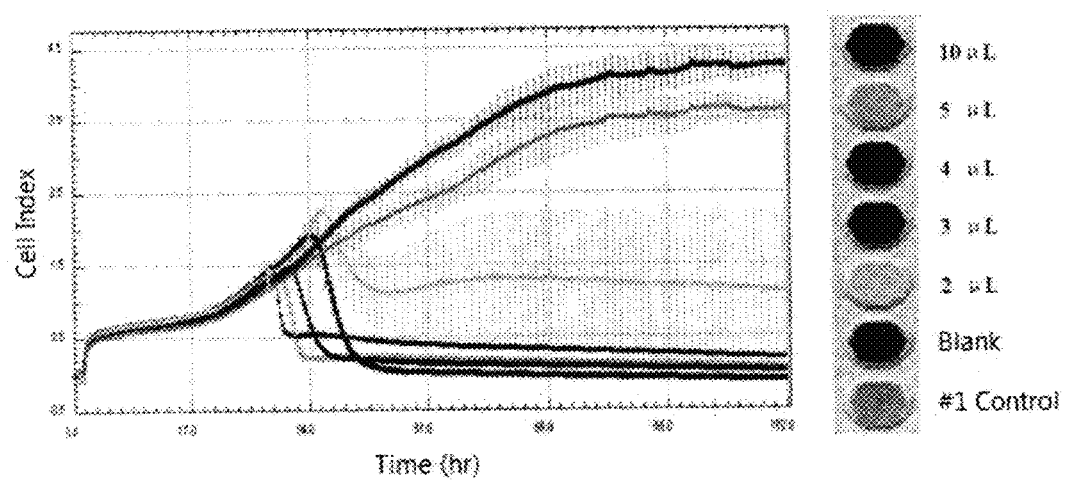

ANTICANCER NANO-SILVER COMPOSITION FOR TREATMENT AND PREVENTION OF CERVICAL CANCER, AND PREPARATION METHOD AND USE THEREOF

FIELD OF THE INVENTION

The present invention relates to a nano-silver composition for the treatment and prevention of cervical cancer, and preparation method and use thereof.

BACKGROUND OF THE INVENTION

Cervical cancer is considered as the most common cause of cancer in women related to female genitals. Cervical cancer occurred more likely in women at the age group between 40 and 55, followed by the age group between 60 and 69. The risk factors of cervical cancer, in the pathogenesis, may include early marriage and child-bearing at a young age, having many sexual partners, and more importantly infection through sexual intercourse with certain types of virus, such as human herpesvirus II, human papillomavirus and human cytomegalovirus, particularly human papillomavirus types 16 and 18 (HPV 16 and HPV 18). Cervical cancer typically develops over 10 to 20 years or even longer, through chronic cervicitis (especially cervical erosion), cervical squamous epithelial dysplasia, carcinoma in situ to invasive cancer.

The morbidity and mortality of cervical cancer are substantial, and, for example, an estimated over 100,000 new cases of cervical cancer occurred each year in China. An estimated over 200,000 deaths from cervical cancer occurred each year globally. Among the young women aged 25 to 45, cervical cancer is the second-most common cause of death from cancer. Due to increasingly more relaxed attitude on sexual activities among women, the incidence of cervical cancer are gradually moved towards younger ages, which may be related to HPV infections and uncontrolled sexual activities, through precancerous changes leading to cervical cancer.

Preventive measures are still globally the most common approach to deal with cervical cancer, such as early treatment of HPV infection or direct injection of HPV vaccine for the prevention of cervical cancer. The HPV vaccines, however, are often too expensive, and treatment of HPV infection may be ineffective due to a delayed finding of the infection, which may be an important reason that the cervical cancer incidences caused by HPV infection remain high in China. Further, cervical cancer is still treated mainly through surgical and chemotherapeutic treatments, which may cause great harms to the body. The treatment of cervical cancer varies worldwide, and, as a result, the recovery rates of cervical cancer differ in various countries, for example, more than 60% in developed countries, and less than 40% in developing or underdeveloped countries, with the overall ratio maintained at the average of more than 50%.

Nano-silver is a type of nano materials. Elemental metallic silver or some silver compounds are treated in physical or chemical method to make nano-scaled metallic silver powder. Due to a high surface area, metallic silver shows some new functions in terms of physical and chemical properties, especially the antibacterial properties. Currently on the market, nano-silver powders are often prepared via chemical methods in varied particle sizes and shapes and with different impurities, and thus it would be difficult to determine the purity, consistency and stability and further the safety of the material. Most of the nano-silver products provided by the manufacturers are of nano-silver being attached on fabric materials to form antibacterial fabrics. Such antibacterial fabrics are then used for various antibacterial purposes, which are of low-level applications. A few domestic manufactures and some foreign manufacturers began to study more precisely the antibacterial properties of nano-silver materials and to develop better performance of nano-silver materials without adversary effects on human body to be used in production of medicines and medical devices, such as sterilization, antibacterial and antibacterial products, masks, gel and suppository.

In recent years, the rapid development of nano-technologies promoted the application of nano materials in the medical field. In the family of the nano materials, nano-silver is a type of elemental silver made with nano structure and high purity, and thus is special in biological functions. High-purity elemental nano-silver has been used in malignant tumor cells in vitro with anti-cancer effects. Also, it was reported that nano-silver is useful in cancer's early stage diagnosis and prognosis monitoring. In the National Institution of High Energy Physics, the scientists for nano biological effects recently discovered that nano-particles after chemical modification demonstrated relatively high efficiency on inhibition on tumor growth without killing the cells directly, which made the immunity enhanced in the mice with tumor and also showed almost no toxicity. It is rather different from traditional antitumor drugs. Experiments indicated that high-purity nano-silver of certain particle sizes and at certain concentrations may achieve the above result, which is desired for the treatment of cancers (Nano Letters, 2013). It is an interesting result for the scientists that such nano-particles need not directly kill the cells, and their distribution in the tumor tissue can be very low, only one over one hundred thousand, for example. Such results suggest that the inhibitory effect of the nano-particles is achieved not by direct killing of the cells and therefore there may be some other unknown anti-cancer mechanisms for further investigation. Nano-technology shall facilitate the discovery effort of new anti-cancer drugs.

Currently, most of the clinical used anti-tumor drugs are highly toxic for killing cells, while killing the tumor cells the drugs also seriously damage the normal cells. The above-mentioned studies avoided such toxicity problem, and thus were considered as of a new approach for the treatment of cancer with high efficiency and low toxicity. However, the above studies used chemically modified nano-particles, which may have drug safety concerns, and further there were no any reports regarding whether the cell killing effect is due to the chemical modification or the nano-particles themselves.

As discussed below, the inventors applied high-purity elemental nano-silver in malignant tumor cells in vitro, and found the anti-cancer effect thereof. The inventors discovered an anticancer nano-silver composition with high purity, high efficacy, high stability and low concentration, and established a drug system of highly dispersible, highly stabilized and readily releasable for drug dispersion, preservation and release and further a method of preparation of such composition.

SUMMARY OF THE INVENTION

To solve the technical problems of the prior art mentioned above, the present invention is directed to provide a nano-silver composition for the treatment and prevention of cervical cancer and method of preparation thereof.

In one aspect, the present invention provided an anticancer nano-silver composition for the treatment and prevention of cervical cancer. The nano-silver composition, on a basis of per kilogram of total weight, includes:
 nano-silver powder 3-200 mg;
 carbomer 700-1,000 mg;
 triethanolamine 700-1,000 mg;
 glucose 2.8-3.2 g;
 water as remaining;
wherein, the purity of silver of the nano-silver powder is ≥99.99%, particles of the nano-silver powder are 1-5 nm in size and are in spherical shape. The nano-silver powder is the No. 5 nano-silver purchased from the Hunan Optics Valley Nano Technology Co., Ltd.

In a further aspect, the present invention provided a method of preparation of the anticancer nano-silver composition. The method includes the following steps:
 (1) Preparing the nano-silver powder, carbomer, triethanolamine, glucose and water in a ratio defined in claim 1;
 (2) adding the carbomer into ½ to ⅔, preferably ⅔, of total amount of the water with mixing; adding the nano-silver powder and the triethanolamine with mixing to obtain a mixture, which is then dispersed in a ultrasonic disperser for 2-5 min;
 (3) adding the glucose and remaining water into the mixture dispersed in step (2) to obtain a mixture, which is then dispersed in a ultrasonic disperser for 1-3 min;
 (4) cooling the mixture dispersed in step (3) to 2-12° C. to obtain a mixture, which is dispersed in an ultrasonic atomizer into a mist, which is collected in a collecting device and is condensed to form an anticancer nano-silver solution;
 wherein, the ultrasonic disperser used in step (2) is of band 2 frequency: 16-24 KHz; the ultrasonic disperser used in step (3) is of band 5 frequency: 40-65 KHz; the ultrasonic atomizer used in step (4) is of band 15 frequency: 120-180 KHz.

The medicament manufactured from the anticancer nano-silver composition to treat and prevent cervical cancer is administrated intravaginally.

The nano-silver powder of the present invention has a spherical shape, high purity (9999) and very high surface activity, and the particles of the powder are 1-5 nm in size. Carbomer and triethanolamine were mixed and used as an excipient, glucose was used as an ion additive, and water was used as a diluent. Carbomer was mixed and diluted with a portion of the water, and the high-purity (9999) spherical nano-silver powder and triethanolamine were added and mixed to form a gelatinous mixture. The resulting mixture was dispersed in an ultrasonic disperser at a band 2 frequency of 16-24 KHz for 2 to 5 minutes, where the spherical nano-silver powder was dispersed evenly with ultrasound; glucose and the rest of the water were added and the resulting mixture was dispersed in the ultrasonic disperser at a band 5 frequency of 40-65 KHz for 1 to 3 minutes, then cooled to 2-12° C.; the resulting mixture was then further dispersed in the ultrasonic disperser at a band 15 frequency of 15 of 120-180 KHz to form a mist material, which was collected in a collecting device and was condensed to form the product as a solution. The product was placed in an opaque plastic container with sealing.

The No. 5 nano-silver powder as used in the invention is of high-purity (99.99) elemental silver nano-particles, and the particles are as required in a spherical shape and 1-5 nm in size. The spherical shape makes the silver nano-particles to be maximal in the specific surface area and stability. If the particle size is greater than 5 nm, as the volume of the particles increases, the unit surface area and activity decrease, and the required drug dosage increases; but if the particle size is less than 1 nm, the manufacturing process would be found quite difficult and very costly. Taking account of drug safety, procedural efficiency and cost-effectiveness, the particle size of the nano-silver powder of the present invention is defined as in the range of 1 nm to 5 nm. The nano-silver composition used in the present invention is highly safe and is of high purity, high efficacy, high stability and low concentration, and it can be manufactured with auxiliary materials through a special process to deliver a drug system of highly dispersible, highly stabilized and readily releasable for drug dispersion, preservation and release.

The experiments showed that the anticancer nano-silver combination of the invention can inhibit HeLa proliferation, and cause cell death, which indicated that the anticancer nano-silver combination can be used to manufacture medicament for the treatment and prevention of cervical cancer. Further, the composition of the invention was prepared from in a specifically designed sequence with multiple dispersing steps, and, as a result, the composition has a high dispersibility and stability as well.

BRIEF DESCRIPTION OF THE DRAWINGS

FIG. 1 illustrates the effects of the anticancer nano-silver solution (containing high-purity (99.99) spherical No. 5 nano-silver) on proliferation of HeLa cells in accordance with an embodiment of the invention.

DETAILED DESCRIPTION OF THE EMBODIMENTS

The nano-silver powder is of the No. 5 nano-silver with a batch number of 2013.05.21-5 as provided by the Hunan Optics Valley Nano Technology Co., Ltd.

Example 1

A nano-silver composition includes on a basis of per kilogram of total weight:
 nano-silver powder 0.2 g;
 carbomer 0.7 g;
 triethanolamine 0.7 g;
 glucose 3 g;
 water 995.4 g;
 wherein, the purity of silver of the nano-silver powder is ≥99.99%, particles of the nano-silver powder are 1-5 nm in size and are in spherical shape.

Example 2

A nano-silver composition includes on a basis of per kilogram of total weight:
 nano-silver powder 0.2 g;
 carbomer 1 g;
 triethanolamine 1 g;
 glucose 2.8 g;
 water 995.195 g;
 wherein, the purity of silver of the nano-silver powder is ≥99.99%, particles of the nano-silver powder are 1-5 nm in size and are in spherical shape.

Example 3

A nano-silver composition includes on a basis of per kilogram of total weight:

nano-silver powder 0.012 g;
carbomer 0.8 g;
triethanolamine 0.8 g;
glucose 3.2 g;
water 995.188 g;
wherein, the purity of silver of the nano-silver powder is ≥99.99%, particles of the nano-silver powder are 1-5 nm in size and are in spherical shape.

Example 4

A nano-silver composition includes on a basis of per kilogram of total weight:
nano-silver powder 0.017 g;
carbomer 1 g;
triethanolamine 1 g;
glucose 3 g;
water 994.983 g;
wherein, the purity of silver of the nano-silver powder is ≥99.99%, particles of the nano-silver powder are 1-5 nm in size and are in spherical shape.

Example 5

A process for preparation of the anticancer nano-silver compositions of the Examples 1 to 4 includes the following steps:

(1) adding carbomer into ⅔ of the total amount of the water with mixing; adding the nano-silver powder and triethanolamine with mixing to obtain a mixture, which is then dispersed in a ultrasonic disperser for 2-5 min;

(2) adding glucose and the remaining water into the mixture dispersed in step (1) to obtain a mixture, which is then dispersed in a ultrasonic disperser for 1-3 min;

(3) cooling the mixture dispersed in step (2) to 2-12° C. to obtain a mixture, which is dispersed in an ultrasonic atomizer into a mist, which is collected in a collecting device and is condensed to form an anticancer nano-silver solution, and the solution was then placed in an opaque plastic container with sealing.

wherein the ultrasonic disperser used in step (1) is of band 2 frequency: 16-24 KHz; the ultrasonic disperser used in step (2) is of band 5 frequency: 40-65 KHz; the ultrasonic atomizer used in step (3) is of band 15 frequency: 120-180 KHz.

Example 6

Experiments were carried out to test the effects of the anticancer nano-silver composition on proliferation of HeLa cells (see FIG. 1).

1. Materials

The anticancer nano-silver composition is that prepared in Example 5 and is marked as high-purity (9999) spherical No. 5 nano-silver.

1. Method

An X-Celligence Real-Time Cell Analysis System was used to generate real time records on the effects of the drug on proliferation of cancer cells within 72 hours after drug administration.

Culture plates of E-Plate are used and in each well of which was placed with 5,000 of cells (initial value), 190 μL of culture medium, and 10 μL of sample solution. Different groups were established with different amounts, i.e., 10, 5, 4, 3 and 2 μL of the sample of the high-purity (99.99%) spherical No. 5 nano-silver, and each group was respectively diluted into 10 μL with a solution of the #1 control group (containing the same solvent as in the No. 5 nano-silver but no nano-silver); there established a #1 control group and a blank group (no interference); and the effects of the high-purity (99.99%) spherical No. 5 nano-silver on the HeLa cell proliferation were observed.

3. Results

The #1 control group showed no any effect for inhibiting the HeLa cell proliferation; the groups of 3 μL (3.675 ppm), 4 μL (4.9 ppm), 5 μL (6.125 ppm) and 10 μL (12.5 ppm) of the No. 5 nano-silver showed complete effects for inhibiting the HeLa cell proliferation, and caused the death of all of the cells; the group of 2 μL (2.5 ppm) showed the effect for inhibiting the HeLa cell proliferation and caused partial death of the cells.

The invention claimed is:

1. A method of treatment of cervical cancer, comprising: administering to a patient in need thereof a therapeutically effective amount of an anticancer nano-silver composition; wherein the anticancer nano-silver composition comprises on a basis of per kilogram of total weight:
nano-silver powder 3-200 mg;
carbomer 700-1000 mg;
triethanolamine 700-1000 mg;
glucose 2.8-3.2 g;
water as remaining;
wherein, purity of silver of the nano-silver powder is ≥99.99%, and particles of the nano-silver powder are 1-5 nm in size;
wherein, the anticancer nano-silver composition is prepared by a method which comprises:

(1) preparing the nano-silver powder, carbomer, triethanolamine, glucose and water in a ratio defined above;

(2) adding the carbomer into ½ to ⅔ of total amount of the water with mixing; adding the nano-silver powder and the triethanolamine with mixing to obtain a mixture, which is then dispersed in a ultrasonic disperser for 2-5 min, wherein the ultrasonic disperser used in this step is of band 2 frequency: 16-24 KHz;

(3) adding the glucose and remaining water into the mixture dispersed in step (2) to obtain a mixture, which is then dispersed in a ultrasonic disperser for 1-3 min, wherein the ultrasonic disperser used in this step is of band 5 frequency: 40-65 KHz; and (4) cooling the mixture dispersed in step (3) to 2-12° C. to obtain a mixture, which is dispersed in an ultrasonic atomizer into a mist, which is collected in a collecting device and is condensed to form an anticancer nano-silver solution, wherein the ultrasonic atomizer used in this step is of band 15 frequency: 120-180 KHz.

2. The method of claim 1, wherein the anticancer nano-silver composition is administrated intravaginally.

3. The method of claim 1, wherein the anticancer nano-silver composition is administrated with an auxiliary material.

* * * * *